US010626206B2

(12) United States Patent
Terrisse (10) Patent No.: US 10,626,206 B2
(45) Date of Patent: Apr. 21, 2020

(54) ACRYLIC COPOLYMER, WHICH IS HYDROPHOBIC, CROSS-LINKED AND BASED ON CINNAMIC ALCOHOL, FOR INTRAOCULAR LENSES

(71) Applicant: ACRYLIAN, Strasbourg (FR)

(72) Inventor: Jean Terrisse, Strasbourg (FR)

(73) Assignee: ACRYLIAN, Strasbourg (FR)

( * ) Notice: Subject to any disclaimer, the term of this patent is extended or adjusted under 35 U.S.C. 154(b) by 18 days.

(21) Appl. No.: 15/769,946

(22) PCT Filed: Nov. 10, 2016

(86) PCT No.: PCT/FR2016/052934
§ 371 (c)(1),
(2) Date: Apr. 20, 2018

(87) PCT Pub. No.: WO2017/081425
PCT Pub. Date: May 18, 2017

(65) Prior Publication Data
US 2018/0312619 A1    Nov. 1, 2018

(30) Foreign Application Priority Data
Nov. 10, 2015  (FR) ...................... 15 60725

(51) Int. Cl.
*A61F 2/16* (2006.01)
*C08F 220/30* (2006.01)
(Continued)

(52) U.S. Cl.
CPC .............. *C08F 220/30* (2013.01); *A61F 2/16* (2013.01); *A61F 2/1613* (2013.01); *A61L 27/16* (2013.01);
(Continued)

(58) Field of Classification Search
CPC ........................................................ A61F 2/16
See application file for complete search history.

(56) References Cited

U.S. PATENT DOCUMENTS 5,702,825 A * 12/1997 Keita ................ C08F 222/1006
428/500
2011/0245442 A1* 10/2011 Terrisse ................ A61F 2/1613
526/227
2016/0331864 A1   11/2016 Acrylian

FOREIGN PATENT DOCUMENTS

WO   2015/128555 A1   9/2015

OTHER PUBLICATIONS

English Translation of Written Opinion of the International Searching Authority for PCT/FR2016/052934 dated May 15, 2018.
(Continued)

*Primary Examiner* — Michael F Pepitone
(74) *Attorney, Agent, or Firm* — Heslin Rothenberg Farley & Mesiti P.C.

(57) ABSTRACT

The material according to the invention is an acrylic copolymer, which is crosslinked, viscoelastic, flexible and deformable at room temperature and hydrophobic, of at least 50 wt % of acrylic or methacrylic monomers and cinnamic alcohol. The mixture of monomers preferably includes: —at least one arylalkoxy-acrylate or one arylalkoxy-methacrylate; at least one hydroxylated acrylate and one hydroxylated methacrylate; at least one ethoxylated diol diacrylate and one ethoxylated diol dimethacrylate; and cinnamic alcohol. Said material is obtained in a single step of radical polymerization and is presented in the form of a three-dimensional macromolecular network including a cinnamic alcohol unit. Said material is used for manufacturing intraocular lenses (1).

20 Claims, 1 Drawing Sheet (51) Int. Cl.
  *A61L 27/16*   (2006.01)
  *G02B 1/04*   (2006.01)
  *C08J 3/24*    (2006.01)
  *C08F 222/10*  (2006.01)

(52) U.S. Cl.
  CPC ............... *C08J 3/24* (2013.01); *G02B 1/041* (2013.01); *G02B 1/043* (2013.01); *A61F 2002/1683* (2013.01); *A61F 2002/1689* (2013.01); *A61F 2210/0057* (2013.01); *A61L 2430/16* (2013.01); *C08F 222/1006* (2013.01); *C08F 2220/301* (2013.01); *C08F 2800/20* (2013.01); *C08F 2810/20* (2013.01); *C08J 2333/14* (2013.01)

(56) References Cited

OTHER PUBLICATIONS

International Search Report (and English translation) and Written Opinion of the International Searching Authority for PCT/FR2016/052934.
Defensive Publication, 896 O.G. 18, T896,013, published Mar. 7, 1972.

\* cited by examiner

ACRYLIC COPOLYMER, WHICH IS HYDROPHOBIC, CROSS-LINKED AND BASED ON CINNAMIC ALCOHOL, FOR INTRAOCULAR LENSES

CROSS REFERENCE TO RELATED APPLICATIONS

This application is a national stage filing under section 371 of International Application No. PCT/FR2016/052934, filed on Nov. 10, 2016, and published on May 18, 2017 as WO 2017/081425, which claims priority to French Application No. 1560725, filed on Nov. 10, 2015. The entire contents of WO 2017/081425 are hereby incorporated herein by reference.

The present invention relates to a new acrylic polymer material that is hydrophobic, viscoelastic, flexible and deformable at room temperature, perfectly suited for producing intraocular lenses.

The invention also relates to a method for manufacturing this polymer material, as well as intraocular lenses made from such a polymer material.

Intraocular lenses are ophthalmological implants or prostheses that are surgically placed in the eye of patients suffering for example from cataracts, to replace their defective crystalline lens.

During this surgical procedure, the surgeon makes a small incision in the patient's cornea, through which he removes the patient's unhealthy natural crystalline lens. Then, through this incision, he places the intraocular lens in the lens bag in place of the removed crystalline lens.

In order for the procedure to be as atraumatic as possible for the patient and to avoid the development of postoperative astigmatism, the incision made in the cornea must be as small as possible.

During the surgical procedure to place the intraocular lens, the lens is rolled on itself in an injector, the outlet end of which is inserted through the incision up to the lens bag.

The intraocular lens, which has a diameter significantly larger than the length of the incision, must be greatly compressed to be able to be expelled through the outlet end of the injector, the outer diameter of which is less than or equal to that of the incision.

Once released into the lens bag, the intraocular lens must deploy quickly and completely to be able to position itself correctly and to be capable of performing its optical correction function in a satisfactory manner.

Due to their nature making them intended to be implanted permanently inside a human eye, the optical function they must perform and their highly restrictive placement method, intraocular lenses are subject to many stresses and must simultaneously fulfill many criteria to be deemed satisfactory.

From an optical perspective, the intraocular lenses must be made from a transparent material with sufficient optical index, i.e., greater than 1.5, capable of focusing on the macula once the lens is placed, while having minimal bulk.

This material must make it possible to perform high precision machining to obtain the necessary optical quality.

Furthermore, the material used must be compatible with permanent implantation of the lenses in the human eye and must not be cytotoxic. It must not, over time, diffuse toxic products so as not to cause inflammation or necroses.

Furthermore, in order for the lens to be able to be placed without difficulty, the material must be flexible enough to be able to be folded and rolled up around itself. It must withstand a significant elongation under the thrust pressure without breaking, or breaking the injection tube, so as to pass through an ejection orifice with an extremely small diameter of about 1.3 mm, or even less than 1 mm.

Lastly, once in the patient's eye, the intraocular lens must be capable of deploying itself on its own in several seconds, without remaining stuck to itself, so that it can position itself correctly in the lens bag and regain its optical characteristics with no trace of plication.

Many intraocular lenses, with varying shapes and compositions, have been proposed in the prior art. However, despite the very wide variety proposed, none to date have succeeded in meeting all of these criteria in a satisfactory manner.

The aim of the invention is to provide a new material making it possible to produce intraocular lenses meeting all of these conditions.

In the prior art, an effort has been made to develop more deformable materials to produce intraocular lenses that are easier to insert through an increasingly small incision.

Lenses made from plastic materials said to be "hydrophilic" have thus been proposed. Although they are more easily deformable, they pose problems in terms of inflammation of the eye, due to the diffusion of products escaping from these lenses that are difficult to purify and always in equilibrium with the water of the eye in which they are implanted.

Furthermore, hydrophilic materials, such as the hydrogels traditionally used for this application, accelerate the migration of the epithelial cells on the surface of the lenses and may thus be responsible, in the long term, for capsular opacification that is particularly bothersome for the patient.

Focus then shifted to plastic materials said to be "hydrophobic", which are conventionally defined by water absorption of less than 5% at 35° C. and which have specific characteristics that do not depend on the quantity of water absorbed. During manufacturing, they can be purified easily and rid of extractable products, which are insoluble or only slightly soluble in water.

These are for example acrylic or silicone-based polymers.

The flexibility of these materials depends on their temperature. They have a glass transition temperature (Tg) below which they are hard and can be machined, and above which they become flexible, deformable and elastic.

To produce intraocular lenses, it is necessary to choose a material having a glass transition temperature low enough that the resulting lens is flexible enough to be rolled and stretched at the temperature of an operating room, i.e. about 18 to 20° C.

The invention falls within the framework of these so-called "hydrophobic" plastic materials, and more specifically targets acrylic polymers.

The well-known problem of these hydrophobic materials is that the more flexible and deformable they are, the stickier they become.

As a result, the intraocular lenses may have trouble deploying correctly when they are implanted in the patient's eye. In particular, their haptics very often remain stuck to the optical part of the lens.

To resolve this technical problem, it has been proposed in the prior art to treat the surface of the lenses, after they are manufactured, to make them more slippery and less sticky. Patent application WO 94/25510 for example proposes, to that end, exposing their surface to a plasma.

An effort has also been made to propose materials that would be more flexible by nature, and not sticky.

Known for example are the copolymers based on acrylates and silicone compounds described in U.S. Pat. No. 8,969,429 B2.

Also known is patent EP 2,285,427, which describes a hydrophobic acrylic polymer material for producing intraocular lenses, which is crosslinked and obtained by radical polymerization.

In order to improve, for this material, the suitability for deformation without breaking at the placement temperatures of the lens, a transfer agent of the thiol type has been added to the mixture of monomers before polymerization of the latter. During polymerization, this transfer agent locally interrupts the formation of the three-dimensional network to create pendant chains. This makes it possible to obtain a more relaxed mesh capable of stretching more without breaking for a high crosslinking rate and elasticity.

The addition of this transfer agent to the mixture thus makes it possible to retain a high crosslinking rate, which contributes to limiting the sticky nature of the resulting polymer, while retaining a significant elongation at break.

However, although this polymer material has undeniable qualities relative to the other commercially available materials, it still has drawbacks that prevent it from resolving the technical problem in a satisfactory manner.

This material is particularly tricky to manufacture. The radical polymerization step necessary for its formation is highly exothermic and the reaction rate must be controlled. The polymerization must be done carefully and under constant monitoring, in order to prevent the reaction from running away, which can be hazardous and which leads to obtaining a lower-quality product.

Indeed, with a transfer agent such as a thiol, the free radicals produced by the peroxide initiator compounds are transferred from the interrupted polymer chain to the remaining monomers. The free radicals accumulate more and more in the reaction mixture, over the course of the decomposition of the peroxides, which accelerates with the increase in temperature caused by the exothermicity of the reaction, and the reaction may run away.

With this type of composition, the appearance is observed of an exothermicity peak that may for example reach up to 180° C. for an initial polymerization setpoint at 80° C.

In order to monitor the reaction rate, one skilled in the art is forced to perform this polymerization at a low temperature (from 50 to 75° C.) and using two different peroxides: a first, rapid peroxide acting at a low temperature until it exceeds a possible critical runaway zone corresponding to about 10 to 15% conversion, then a second, slower peroxide that acts at a higher temperature to complete the reaction.

All of these precautions, in particular the low reaction temperature, having to be maintained at the beginning of the reaction, explain why this manufacturing step lasts a particularly long time, i.e., generally between 10 and 15 hours for the polymerization. This substantial duration constitutes a major drawback for the industrialization of the production of such a material, since it greatly limits the general productivity that can be obtained. It is in fact difficult to perform more than one production cycle per day.

Furthermore, the thiols used as transfer agents in this prior patent are sulfur chemical compounds that are particularly unpleasant to use due to their strong, nauseating odor.

One aim of the invention is to offer an alternative to the use of these thiols, and more generally to the use of transfer agents, to manufacture an acrylic polymer material suitable for producing intraocular lenses that preserves the advantages of this material described in the prior art.

Another aim of the invention is to provide a new material that could be manufactured more easily and much more quickly, without having the drawbacks cited above.

It is therefore not a matter of finding a simple equivalent for the transfer agent, but obtaining a different, much more advantageous material.

The invention thus offers a different solution to the technical problem by teaching a new acrylic polymer material, which is flexible and elastically deformable at room temperature, hydrophobic and crosslinked, for manufacturing intraocular lenses, which is obtained in a single radical polymerization step, without using a transfer agent, and which is much more practical to manufacture, with a significantly higher productivity.

To that end, the invention provides an acrylic polymer material, which is hydrophobic, suitable for producing intraocular lenses, which is characterized in that it is a copolymer that is crosslinked, viscoelastic, flexible and deformable at room temperature, of a mixture of monomers comprising at least 50 wt % of acrylic or methacrylic monomers and cinnamic alcohol.

The polymer material according to the invention is an acrylic material, i.e., it is mainly made up from acrylic and/or methacrylic monomers.

It is a copolymer of a mixture of monomers containing, in addition to the cinnamic alcohol, at least 50 wt %, preferably at least 80 wt %, and still more preferably at least 90 wt % of one or more acrylic or methacrylic monomers.

This mixture of monomers preferably comprises at least:
an arylalkoxy-acrylate or an arylalkoxy-methacrylate;
a hydroxylated acrylate and a hydroxylated methacrylate;
an ethoxylated diol diacrylate and an ethoxylated diol dimethacrylate; and
cinnamic alcohol.

Cinnamic alcohol refers to the chemical compound with the formula below:

In the literature, there are many other names for this compound, in particular: 3-phenyl-2-propen-1-ol, 3-phenyl-2-propenol, phenyl-3-propene-2-ol-1, 2-propen-1-ol 3-phenyl, styrolic alcohol, cinnamyl alcohol, styrone, styryl alcohol, phenyl-3 allyl alcohol, 3-phenyl-allyl alcohol, γ-phenyl-allyl alcohol, vinyl-phenyl-carbinol, styryl-carbinol.

Surprisingly, and although it does not comprise any thiol or other transfer agent, the obtained crosslinked polymer is viscoelastic, flexible and elastically, i.e., reversibly, deformable at room temperature, without being sticky. It can deform easily and without breaking at the placement temperatures of the lens, and can therefore be rolled and stretched without problem to be implanted in a patient's eye.

In this patent application, a material is considered to be flexible and deformable at room temperature when its glass transition temperature (Tg) is less than 15° C. and its elastic modulus at 25° C. is less than 5 MPa after a relaxation time greater than 30 seconds.

One can see that unexpectedly, the presence of cinnamic alcohol among the monomers makes it possible to decrease the elastic modulus of the obtained crosslinked copolymer, at a constant crosslinking agent level. The cinnamic alcohol thus makes it possible to obtain a three-dimensional macromolecular network that has a significant elongation at break even with a high crosslinking rate, even when no transfer agent is present in the mixture.

The cinnamic alcohol makes it possible to obtain a result similar to that of the thiol-type compounds of the prior art, but acts completely differently.

Indeed, unlike the thiol-type compounds of the prior art, cinnamic alcohol is a monomer that, for the molecules having reacted, bonds to the macromolecular network being formed. It is therefore not a transfer agent that remains free in the reaction mixture and is not part of the formed polymer.

Furthermore, while transfer agents capture the free radicals temporarily to transfer them from one macromer, which may or may not be crosslinked, to another monomer, thus moving the polymerization location without decreasing the number of free radicals circulating in the reaction mixture, the cinnamic alcohol monomer seems to work under a different mechanism.

It has been noted that the exothermicity of the reaction remains limited, and there are no longer any hazardous exothermicity peaks. The reaction no longer risks running away.

The cinnamic alcohol monomer seems to capture the macromer free radicals lastingly and stably, thus leading to a gradual decrease in the number of free macroradicals present once they are bonded. Such a mechanism is compatible with the observation that very little cinnamic alcohol introduced into the mixture is consumed.

The polymerization can therefore be done without any special precautions, with a single peroxide (rapid peroxide in sufficient quantity) and at a temperature allowing a full conversion in several hours (for example, around 90 to 110° C.), with no exothermicity peak or risk of running away.

At such a temperature, the duration of this polymerization can be limited to about 2 to 6 hours, which is significantly below the durations of 10 to 15 hours necessary with the transfer agents of the prior art. The manufacturing productivity is improved greatly as a result.

Furthermore, this manufacturing is less tricky and complex for operators to carry out, due to much less critical precautions to be taken.

This significant improvement in productivity, combined with the simplification of the implementation of the manufacturing method, is a considerable advantage for industrializing the manufacture of the material according to the invention relative to the materials of the prior art.

Furthermore, cinnamic alcohol is much more pleasant to use than the sulfur compounds used in the prior art, since it does not have their nauseating odor. Operator comfort is thus improved.

Cinnamic alcohol is therefore not a mere equivalent for the transfer agent, since it is of a different nature, acts differently, and further procures considerable advantages during manufacturing.

The invention also provides an intraocular lens, to be implanted surgically in the lens bag of a patient to replace the latter's natural crystalline lens, which is advantageously made from an acrylic polymer material as described above.

The invention lastly teaches a method for manufacturing this acrylic polymer material, which comprises the following steps:
  producing a mixture of monomers containing at least 50 wt % of acrylic or methacrylic monomers and cinnamic alcohol, this mixture comprising at least one crosslinking monomer;
  adding at least one initiator compound to said mixture;
  performing radical polymerization of said mixture, in a single polymerization step, so as to obtain, through this polymerization, an acrylic or methacrylic copolymer that is crosslinked, viscoelastic, flexible and deformable at room temperature, and comprising cinnamic alcohol.

According to one preferred embodiment of the invention, this method further comprises a purification step, preferably leaching, making it possible to reduce the quantity of extractable products in the final product.

Other features and advantages of the invention will appear upon reading the following detailed description, in particular the role, preferred nature and quantity of each of the monomers and other components of the mixture making it possible to obtain the material according to the invention.

To facilitate proper comprehension for the reader, this description is accompanied by the following exemplary appended drawings.

Figure 1:
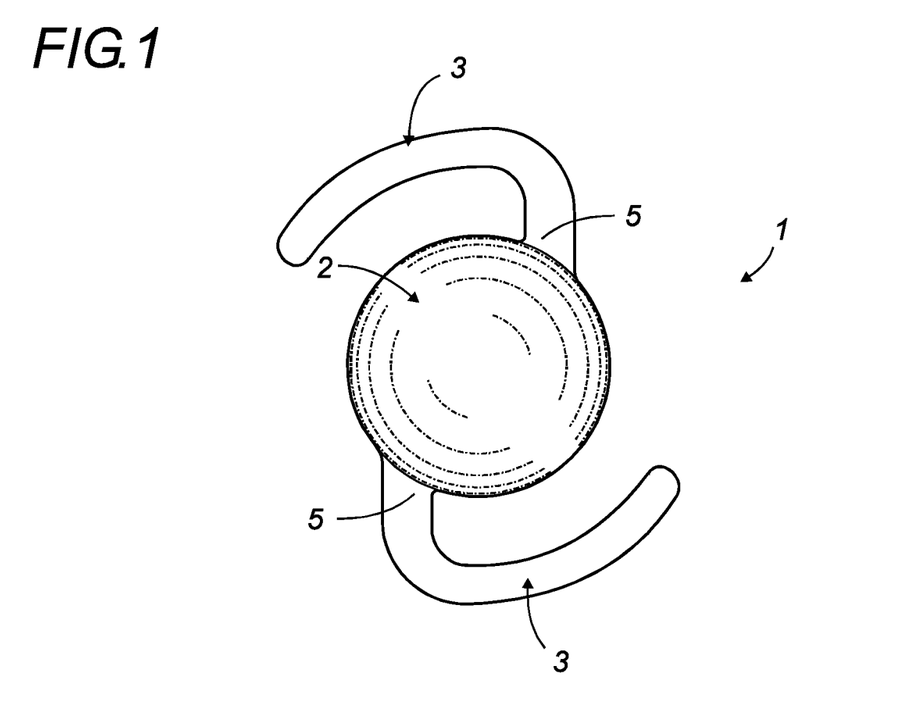
FIGS. 1 and 2 are schematic views of two traditional examples of an intraocular lens that can be made from the material according to the invention.
Figure 2:
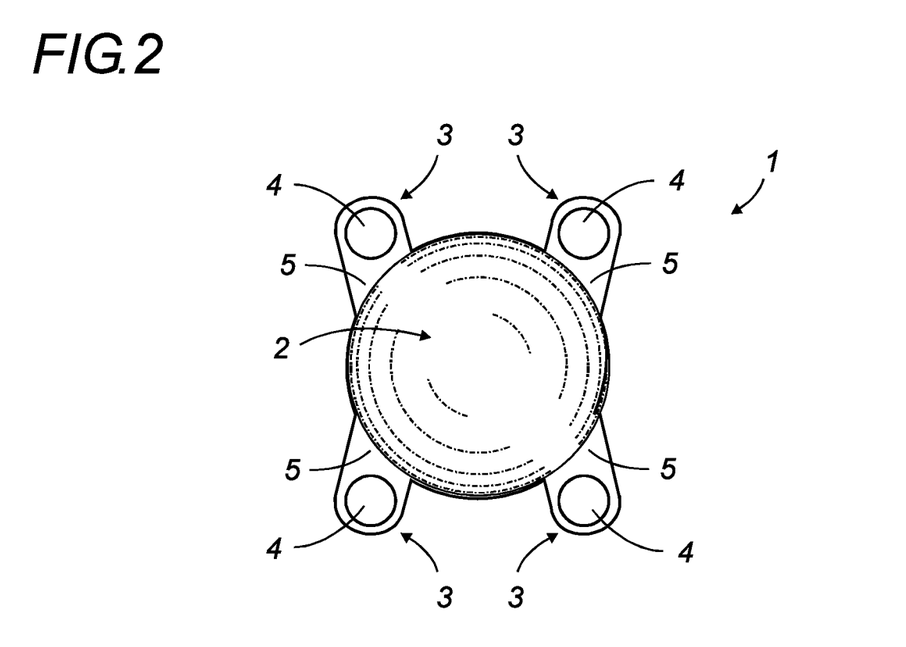

These lenses 1 traditionally comprise a central optical part 2, substantially disc-shaped and with a profile that is most often biconvex. This corrective optical part 2 must be positioned perpendicularly and centered relative to the optical axis of the eye.

Extending from this optical part 2 are lateral projections called haptics 3, whose role is to stretch the walls of the lens bag and provide correct positioning of the lens relative to the said walls.

In FIG. 1, there are two of these haptics 3. They are positioned so as to be diametrically opposite and have a curved arm shape each going in an opposite direction.

The lens of FIG. 2 comprises four haptics 3 in the form of a ring pierced by a central orifice 4. These haptics 3 are regularly distributed on the perimeter of the optical part 2.

The haptics 3 are connected to the central optical part 2 by a junction zone 5 forming a hinge that creates a spring effect by elastic return of the material to unfold the lens when it is implanted in a patient's eye.

In the illustrated examples, the haptics 3 are made in one piece with the optical part 2 of the lens 1. This type of lens is called a "single-piece lens".

The material according to the invention is particularly suitable for producing such intraocular lenses 1.

The inventor has surprisingly noted that the cinnamic alcohol monomer appears to play a singular role, but with a reactivity that is advantageously very low, in the compositions of acrylic and/or methacrylic monomers.

By carrying out the polymerization of many compositions containing acrylic and/or methacrylic monomers and cinnamic alcohol in order to obtain crosslinked copolymers, several surprising observations have been made, namely that:
  the cinnamic alcohol monomer was consumed little relative to the introduced mass,
  the kinetics of the reaction were modified to the point of practically eliminating the exothermicity peak, which was very present with the transfer agents,
  the chemical nature of the obtained product is only very slightly modified by the presence of cinnamic alcohol monomers, and
  the mechanical properties of the obtained product are profoundly modified, despite the small quantity of cinnamic alcohol monomers consumed.

From these observations, the inventor proposed the general interpretation, which is consistent with each of these observations, that the cinnamic alcohol monomer appeared to play a chain-terminating role, but with a reactivity that is advantageously very low.

Indeed, the absence of exothermicity peak can be interpreted as being related to a disappearance of free radicals (very different from the accumulation of free radicals caused by the transfer agents of the prior art), and the incidence on the mechanical properties to the production of pendant chains by the termination reaction. The low consumption of the cinnamic alcohol monomer and the fact that it is limited to a chain end position would explain why the chemical properties of the obtained polymer are only very slightly modified.

Surprisingly, the cinnamic alcohol monomer has a particular reactivity, different from that which one skilled in the art could expect by generalizing the behavior of the other members of the family of allyl compounds or the styrene family.

The inventor has in fact tested numerous compounds belonging to these allyl and styrene families, in particular α-methyl-styrene, vinyl toluene, allyl alcohol and esters, without obtaining satisfactory results for the manufacture of a polymer material for intraocular lenses.

He noted that during the free-radical polymerization step, these allyl or styrene compounds, once attached to the macromolecular network, continue to polymerize, either by co-polymerization with the other monomers or, for some, at the end of reaction by homopolymerization with identical molecules, and are thus inserted inside the network. The structure and the chemical nature of the obtained network are modified in a manner that is sufficient to change the chemical and physical properties, in particular the optical properties, of the resulting polymer material, making it unsuitable for producing intraocular lenses.

Cinnamic alcohol has a particular structure, comprising an aromatic core conjugated with a double allyl bond, which gives it an unexpected behavior different from that of products in the same family.

Unlike the other allyl compounds, the radical created at the double bond of the cinnamic alcohol appears to be very stable and stops the copolymerization of the species present on the chain having captured a cinnamic alcohol monomer. Cinnamic alcohol monomers are therefore not very present within the resulting macromolecular network, and their influence on the chemical properties of the overall network remains limited. It therefore has no significant impact on the chemical properties of the macromolecular network and for the manufacture of intraocular lenses.

Conversely, by locally interrupting the formation of the three-dimensional mesh, the cinnamic alcohol monomers behave like terminating agents and form where they are a cut mesh with a short pendant chain connected to the network, but where the other cinnamic alcohol end remains free. Through the creation of these localized pendant chains, they thus make it possible to obtain a more relaxed mesh, i.e., a network with a low elastic modulus, capable of stretching more without breaking.

Traditional terminating agents, such as free-radical scavengers of the quinonic or quinoline stabilizing type, have also been tested. However, the tested compounds also have not made it possible to obtain satisfactory results for manufacturing a polymer material for intraocular lenses.

Indeed, these compounds very quickly capture most of the free radicals present in the reaction medium. Even added in very small quantities, they quickly cause the polymerization to stop, the latter ultimately only forming several small macromers, and not the desired crosslinked macromolecular network.

To be able to use such compounds effectively, an extremely small quantity, measured very precisely, should be added. This is clearly incompatible with the desired industrial manufacturing.

Advantageously, the cinnamic alcohol only has a very low yield as comonomer. Indeed, from 50 to 80% of the cinnamic alcohol introduced into the reaction mixture is not captured by the macromers and remains present in the free state at the end of polymerization.

It can therefore be added in an easily measurable and manipulable quantity, compatible with an industrialized method, without causing the polymerization to stop completely, or leading to the creation of an excessive number of pendant chains.

Once the polymerization is complete, the cinnamic alcohol monomers that have not reacted and all the other residual monomer compounds or the like, not bound to the network, are extracted from the obtained polymer by a simple purification step, for example leaching.

To obtain a satisfactory result, a quantity of cinnamic alcohol is preferably used comprised between 0.1 wt % and 5 wt %, more preferably between 0.2 wt % and 2 wt %, and preferably substantially equal to 0.5 wt %, of the mixture of monomers.

Other compounds in the same family as cinnamic alcohol have also been studied, but have not been selected. Cinnamic aldehyde is thus too toxic to be able to be used in intraocular lenses. Cinnamate esters, obtained by esterifying cinnamic acid with various alcohols containing from 1 to 12 carbons, were tested, but did not prove effective during polymerization. They did not make it possible to reduce the exothermicity peak and did not give the resulting polymer material the expected properties. Likewise, esters of cinnamic alcohol with acids such as acetic acid, benzoic acid or the like, did not have a significant impact on the reaction comparable to that obtained with cinnamic alcohol.

Due to its unexpected behavior, it appears that the advantageous choice of the cinnamic alcohol monomer to produce a polymer material according to the invention is not an arbitrary, typical or obvious choice for one skilled in the art. This compound, which is used very little in this technical field, shows surprising behavior and imparts decisive advantages for manufacturing the polymer.

Preferred examples of other monomers that can be used to obtain a material according to the invention will now be described.

Among acrylic and/or methacrylic monomers, at least one arylalkoxy-acrylate and/or arylalkoxy-methacrylate will be preferentially used in order to obtain a final polymer with a high optical index.

It is possible to use, as arylalkoxy-acrylate, a compound chosen from among ethoxylated phenoxy-acrylates comprising from one to six ethoxylated functions, such as 2-phenoxy-(2-ethoxy)n-acrylate with $1 \leq n \leq 6$, and preferably $1 \leq n \leq 4$.

One preferred example is 2-phenoxy-ethylacrylate (n=1), commonly called 2PEA, and 2-phenoxy-(2-ethoxy)$_4$-acrylate, usually called 4PEA, or a mixture of these two monomers.

When it is used, 4PEA advantageously makes it possible to decrease the glass transition temperature of the resulting polymer, while giving it a certain hydrophilicity to cause the tendency of the surfaces to stick to themselves to decrease.

It also contributes to reducing glistening, i.e., the sensitivity to whitening of the obtained polymer material.

For the arylalkoxy-methacrylate, one may for example choose 2-phenoxy-ethylmethacrylate, 2-phenoxy-2-ethoxy-ethylmethacrylate, 2-phenoxy-2-ethoxy-2-ethoxy-ethyl-methacrylate and its higher oligomers.

However, arylalkoxy-acrylates are generally preferred to arylalkoxy-methacrylates because they have a lower glass transition temperature.

It is also possible to use a mixture of several of these compounds.

The mixture of monomers preferably comprises between 50 and 90 wt % of arylalkoxy-acrylate and/or arylalkoxy-methacrylate. Preferably, it contains between 70 and 85 wt %.

In the cited preferred case of a mixture of 2PEA and 4PEA, there will preferably be 65 to 75% of 2PEA and 6 to 20% of 4PEA.

Another preferred example embodiment contains only 2PEA.

The mixture of monomers also preferably contains at least one hydroxylated acrylate and one hydroxylated methacrylate.

These hydroxylated monomers increase the surface tension and the surface affinity with water of the resulting polymer, which decreases the stickiness of the material, in particular when water is present. They also contribute to decreasing the glistening phenomenon.

These effects are further enhanced by the presence of the cinnamic alcohol monomer terminating the chains, which increases the overall quantity of alcohol functions present at the chain ends.

The hydroxylated acrylate used is for example a dihydroxy-alkyl monoacrylate or a dihydroxy-ethoxy-alkyl monoacrylate whose glycol alkyl chain comprises from 2 to 6 carbon atoms. Examples include 4-hydroxy-butyl-acrylate, also called butanediol monoacrylate or 4HBA, hydroxyethyl acrylate or HEA, hexanediol monoacrylate, or triethylene glycol monoacrylate.

The hydroxylated methacrylate used is preferably a dihydroxy-alkyl monomethacrylate or a dihydroxy-ethoxy-alkyl monomethacrylate whose glycol alkyl chain comprises from 2 to 6 carbon atoms. This is for example hydroxy-ethyl-methacrylate or HEMA, propanediol monomethacrylate, butanediol monomethacrylate, hexanediol monomethacrylate or triethylene glycol monomethacrylate.

The proportion of these hydroxylated monomers in the mixture before polymerization must be sufficient for the resulting material to have an appropriate surface tension and not to whiten in prolonged contact with water at 35° C. It must, however, be limited so that the resulting material remains globally hydrophobic and does not absorb more than 5% water at 35° C., as agreed for so-called hydrophobic products.

Advantageously, the hydroxylated acrylate and the hydroxylated methacrylate together preferably make up between 8 and 35 wt % of the mixture of monomers, and more preferably between 15 and 30 wt % of the mixture.

The relative proportion of these two hydroxylated monomers with respect to one another may vary depending on the case from 20 to 80% for one and the reverse for the other, as a function of the desired glass transition temperature.

One preferred polymer example according to the invention may thus for example comprise from 15 to 20% of acrylic alcohol of the HEA or 4HBA type and 4 to 8% of methacrylic alcohol of the HEMA type.

The mixture also contains crosslinking compounds making it possible to obtain, after polymerization, a three-dimensional macromolecular network, and not linear polymers. They are preferably difunctional monomers of the ethoxylated diol diacrylate and ethoxylated diol dimethacrylate type.

These crosslinking compounds preferably comprise ethoxy functions so as not to increase the glass transition temperature of the final material and at the same time to maintain a homogeneous hydrophilicity level with the rest of the composition.

The ethoxylated diol diacrylate and the ethoxylated diol dimethacrylate preferably used are in particular polyethylene glycol diesters comprising from 2 to 5 ethoxyl functions, preferably tetraethylene glycol diacrylate and tetraethylene glycol dimethacrylate.

Advantageously, the ethoxylated diol diacrylate and ethoxylated diol dimethacrylate together preferably make up between 1 and 3 wt % of the mixture of monomers, the relative proportion between the ethoxylated diol diacrylate and the ethoxylated diol dimethacrylate preferably varying from 25 to 75% relative to one another, and vice versa.

It is also possible to add, among the monomers, one or more dye(s), which may or may not be polymerizable, or one or more anti-UV agent(s), whose function within the final material is to absorb ultraviolet rays. This may for example be 2-[3-(2H-benzotriazol 2 yl)-4-hydroxyphenyl]ethyl-methacrylate, which is preferably used in a proportion comprised between 0.1 wt % and 1 wt %, and for example with a content of 0.5%.

One then obtains a crosslinked copolymer of at least the aforementioned monomers and a UV-absorbing monomer.

Any other monomer or any other polymerizable or non-polymerizable component imaginable by one skilled in the art, with any function, may be added into the mixture without going beyond the scope of the present invention, as long as its presence does not alter the general properties of the resulting polymer material in a manner that makes it unsuitable for manufacturing intraocular lenses.

Examples include adding a yellow dye, for example an acrylic or methacrylic derivative of a polymerizable dye.

In addition to these monomers, the initial mixture may contain a certain number of additional compounds of different natures, for example necessary for the reaction to progress correctly.

It thus comprises one or more, but preferably only one, initiator compound used to initiate the polymerization reaction by creating active sites on the monomers.

This initiator compound is preferably a peroxide, chosen as a function of its half-life time having to allow rapid and controllable polymerization under the selected conditions for the polymerization of the material according to the invention, and as a function of the purity of the commercially available product.

This peroxide may be chosen from among acyl-peroxides, alkyl-peroxides and peroxyesters and peroxycarbonates. Examples of these products include, but are not limited to, tert-amyl-peroxy-2-ethyl-hexyl-carbonate also called Taec, tert-butyl-peroxy-2-ethyl-hexanoate, 1,1-ditertio-butyl-per-oxy-3,3,5-trimethylcyclohexane, 1,1-ditertio-butyl-peroxy-cyclohexane, tertio-butyl-peroxy-3,3,5-trimethylhexanoate, tertiobutyl-peroxy-isopropylcarbonate, dicumyl-peroxide, tert-butylcumyl-peroxide, di-tert-amyl-peroxide, tert-butyl-3-isopropenyl-cumyl-peroxide, dioctananoyl-peroxide, didecanoyl-peroxide, tert-butyl-peroxy-2-ethylhexanoate, tert-amyl-peroxy-2-ethylhexanoate, tert-butyl-peroxy-3,5,5-trimethylhexanoate, 2,5-dimethyl-2,5-di(benzoylperoxy)

hexane, tert-amyl-peroxyacetate, tert-butyl-peroxypivalate, tert-amyl-peroxypivalate, tert-butyl-peroxybenzoate, tert-amyl-peroxybenzoate; tertio-butyl-peroxy-2-ethylhexyl carbonate, tertio-amyl peroxy-2-ethylhexyl carbonate, or tertio-butyl-peroxy-isobutyrate.

This compound or compounds are added to the mixture in a very small quantity, the mixture for example comprising between 0.3 and 2 wt % of initiator compound.

The polymerization temperature is determined by the half-life time of the selected peroxide on the one hand, and the targeted polymerization duration on the other hand, typically so as to combine 2 to 6 half-life times.

By summarizing the above considerations, it is possible to imagine a specific mixture of monomers leading, by radical polymerization, to a preferred embodiment of the material according to the invention, but without limiting the invention thereto.

This mixture preferably comprises at least the following monomers: 2-phenoxy-ethylacrylate, 2-phenoxy(-2-ethoxy)$_4$-acrylate, 4-hydroxy-butyl-acrylate and/or hydroxy-ethyl-acrylate, hydroxy-ethyl-methacrylate, tetraethylene glycol diacrylate, tetraethylene glycol dimethacrylate, and cinnamic alcohol.

In order to make this description more complete, we will now describe an example of a method for obtaining an acrylic polymer material according to the invention from the preferred initial mixture outlined above.

To achieve the desired polymerization, first all of the monomers necessary for the reaction are mixed together, including the cinnamic alcohol. Advantageously, these monomers are soluble in one another and simple agitation suffices to produce a homogeneous mixture.

Next, the initiator compound necessary to initiate the polymerization reaction is added to this mixture.

Then the radical polymerization is carried out in a single step.

This is a solvent-free mass polymerization with all of the reagents present from the beginning, in appropriate amounts to obtain the final polymer with all of the desired properties, in a single operation.

It is therefore not necessary, like in some examples of the prior art, to produce a viscous pre-polymer, molded in a second operation.

To that end, small quantities of the mixture of monomers are advantageously placed in molds and heated for example to a temperature comprised between 90 and 110° C. for 3 to 6 hours.

Once the reaction is complete and after cooling, the polymer is stripped.

Such polymerization durations make it possible to perform several daily molding cycles with the same mold.

The molds are preferably chosen so as to obtain, after stripping, polymer blocks that are low-height and generally cylindrical, of the "chip" or "puck" type. Such a shape is perfectly suited for subsequent machining of these polymer blocks in order to obtain the intraocular lenses.

Of course, direct molding of the intraocular lenses is also possible with an appropriate mold.

The polymer blocks are next purified, in order to rid them of the monomers that did not react, in particular the cinnamic alcohol, and of impurities and residual products in particular coming from the synthesis of each of the monomers used. This purification can preferably be done by leaching.

After this purification step, a material is obtained that has the physical properties indicated in this application.

The blocks of polymer material are then ready to be machined, at a temperature below the glass transition temperature of the polymer, to produce the intraocular lenses according to the invention.

In order to perfectly describe the invention, several examples of acrylic polymer material according to the invention are described below.

The acrylic polymer materials were obtained by radical polymerization from the following mixtures of monomers, the quantities of which are expressed in weight percentages of the mixture of monomers before polymerization.

In all of the examples below, the mixture of monomers was heated gradually for a duration of 1.5 hours to go from room temperature to 90° C. It was next kept at 90° C. for 1 hour to go from liquid state to gel state, then heated to 110° C. for 3 hours.

No exothermicity peak was observed throughout the entire polymerization duration, in particular during the passage from the liquid state to the gel state.

EXAMPLE 1

| MONOMERS: | wt % |
|---|---|
| 2-phenoxy-ethylacrylate | 77.2% |
| 2-phenoxy-(2-ethoxy)$_4$ acrylate | 6% |
| 4-hydroxy-butyl-acrylate | 9.7% |
| hydroxy-ethyl-methacrylate | 4% |
| tetraethylene glycol diacrylate | 0.6% |
| tetraethylene glycol dimethacrylate | 2.0% |
| cinnamic alcohol | 0.5% |

The polymerization reaction is triggered by adding 0.5% of TAEC. After polymerization, an acrylic polymer material is obtained with an optical index equal to 1.5381, a glass transition temperature equal to 7.5° C. and an elastic modulus of 0.658 MPa at 25° C. after one minute of relaxation.

EXAMPLE 2

| MONOMERS: | wt % |
|---|---|
| 2-phenoxy-ethylacrylate | 68.7% |
| 2-phenoxy-(2-ethoxy)$_4$ acrylate | 6% |
| hydroxy-ethyl-acrylate | 15.3% |
| hydroxy-ethyl-methacrylate | 7.7% |
| tetraethylene glycol diacrylate | 0.45% |
| tetraethylene glycol dimethacrylate | 1.35% |
| cinnamic alcohol | 0.5% |

The polymerization reaction is triggered by adding 0.5% of TAEC. After polymerization, an acrylic polymer material is obtained with an optical index equal to 1.540, a glass transition temperature equal to 12.4° C. and an elastic modulus of 0.51 MPa at 25° C. after one minute of relaxation.

EXAMPLE 3

| MONOMERS: | wt % |
|---|---|
| 2-phenoxy-ethylacrylate | 61.4% |
| 2-phenoxy-(2-ethoxy)$_4$ acrylate | 13% |
| 4-hydroxy-butyl-acrylate | 16.5% |

-continued

| MONOMERS: | wt % |
|---|---|
| hydroxy-ethyl-methacrylate | 6.8% |
| tetraethylene glycol diacrylate | 0.45% |
| tetraethylene glycol dimethacrylate | 1.35% |
| cinnamic alcohol | 0.5% |

The polymerization reaction is triggered by adding 0.5% of TAEC. After polymerization, an acrylic polymer material is obtained with an optical index equal to 1.5390, a glass transition temperature equal to 6.3° C. and an elastic modulus of 0.495 MPa at 25° C. after one minute of relaxation.

EXAMPLE 4

| MONOMERS: | wt % |
|---|---|
| 2-phenoxy-ethylacrylate | 74.4% |
| 4-hydroxy-butyl-acrylate | 16.5% |
| hydroxy-ethyl-methacrylate | 6.8% |
| tetraethylene glycol diacrylate | 0.45% |
| tetraethylene glycol dimethacrylate | 1.35% |
| cinnamic alcohol | 0.5% |

The polymerization reaction is triggered by adding 0.5% of TAEC. After polymerization, an acrylic polymer material is obtained with an optical index equal to 1.5420, a glass transition temperature equal to 11.2° C. and an elastic modulus of 0.550 MPa at 25° C. after one minute of relaxation.

EXAMPLE 5

| MONOMERS: | wt % |
|---|---|
| 2-phenoxy-ethylacrylate | 72.4% |
| 4-hydroxy-butyl-acrylate | 17.9% |
| hydroxy-ethyl-methacrylate | 7.4% |
| tetraethylene glycol diacrylate | 0.45% |
| tetraethylene glycol dimethacrylate | 1.35% |
| cinnamic alcohol | 0.5% |

The polymerization reaction is triggered by adding 0.5% of TAEC. After polymerization, an acrylic polymer material is obtained with an optical index equal to 1.5420, a glass transition temperature equal to 10° C. and an elastic modulus of 0.510 MPa at 25° C. after one minute of relaxation.

Upon reading all of these examples, one can see that in order to obtain the polymer material according to the invention, the polymerization duration is much shorter than in the prior art, and it is done with no exothermicity peak, and therefore with no risk of running away.

In order to demonstrate the surprising and particularly advantageous properties imparted by cinnamic alcohol to the material according to the invention regarding its suitability for deformation without breaking at the usage temperatures, the table below shows the composition and the elastic modulus E, expressed in MPa and measured after 60 seconds at a temperature of 25° C., for different acrylic polymer materials, intended to produce intraocular lenses.

| No. of the tested formula | Composition in percentage by weight | | | | | | | | Elastic modulus E in MPa, after 60 s at 25° C. |
|---|---|---|---|---|---|---|---|---|---|
| | 2PEA | 4PEA | 4HBA | HEMA | TDIA | TDIMA | CA | Thiol | |
| 1 | 77.6 | 6.0 | 9.7 | 4.0 | 0.6 | 2.0 | 0.1 | | 0.814 |
| 2 | 77.2 | 6.0 | 9.7 | 4.0 | 0.6 | 2.0 | 0.5 | | 0.658 |
| 3 | 76.7 | 6.0 | 9.7 | 4.0 | 0.6 | 2.0 | 1.0 | | 0.561 |
| 4 | 74.7 | 6.0 | 9.7 | 4.0 | 0.6 | 2.0 | 3.0 | | 0.460 |
| 5 | 72.7 | 6.0 | 9.7 | 4.0 | 0.6 | 2.0 | 5.0 | | 0.348 |
| 6 | 77.7 | 6.0 | 9.7 | 4.0 | 0.6 | 2.0 | | 0.1 | 0.819 |
| 7 | 77.7 | 6.0 | 9.7 | 4.0 | 0.6 | 2.0 | | | ≈0.90* |

Formulas 1 to 5 correspond to materials according to the invention containing cinnamic alcohol (CA) in their composition.

Formula 6 corresponds to a formula not containing cinnamic alcohol, but in which, according to the prior art, a transfer agent of the thiol type has been added to the mixture of monomers.

Formula 7 corresponds to a reference material not containing cinnamic alcohol or thiol.

The abbreviations used in the table have the following meanings:
2PEA: 2 phenoxy-ethylacrylate
4PEA: 2-phenoxy-(2-ethoxy)4 acrylate
4HBA: 4-hydroxy-butyl-acrylate
HEMA: hydroxy-ethyl-methacrylate
TDIA: tetraethylene glycol diacrylate
TDIMA: tetraethylene glycol dimethacrylate
CA: cinnamic alcohol
*: Material rejected from the study, since it has many cracks and is unsuitable for producing intraocular lenses. Its elastic modulus was not able to be measured precisely.

In order to be able to assess the influence of cinnamic alcohol on the elasticity of the resulting material, the different tested formulas have a very similar composition. The relative proportion of the monomers is identical, with the exception of cinnamic alcohol and 2PEA, which varies accordingly to adjust the total of the monomers to 100%.

Formula no. 6 contains a thiol in addition to monomers.

When viewing the table, one can see that the more one increases the quantity of cinnamic alcohol, the more the elastic modulus of the obtained material decreases, while the crosslinking rate is also kept constant (same quantities of TDIA and TDIMA used).

The addition of cinnamic alcohol in an acrylic medium therefore indeed makes it possible to improve, adapt or adjust the elasticity of the obtained polymer material, without being obligated to decrease the crosslinking agent level.

For formula 1, this effect is similar to that obtained with the thiol-type transfer agent in formula 6. It is even greater in all of the other tested formulas 2 to 5.

One can also see that adding cinnamic alcohol improves the situation considerably relative to formula no. 7. Indeed, with reference formula 7 containing neither cinnamic alcohol nor thiol, an extremely brittle product was obtained, which did not withstand the stresses caused by the volume shrinkage related to polymerization under the selected conditions and in which many cracks formed, making it inappropriate for the targeted application.

Obviously, the invention is not limited to the preferred embodiments described above and shown in the various figures, a person skilled in the art being able to make numerous modifications and imagine other embodiments without going beyond the framework and scope of the invention as defined in the appended claims.

The invention claimed is:

1. An acrylic polymer material, which is hydrophobic, wherein the acrylic polymer material is a copolymer that is crosslinked, viscoelastic, flexible and deformable at room temperature, of a mixture of monomers comprising at least 50 wt % of acrylic or methacrylic monomers and cinnamic alcohol, wherein the acrylic polymer material has a glass transition temperature (Tg) less than 15° C. and an elastic modulus at 25° C. less than 5 MPa after a relaxation time greater than 30 seconds.

2. The acrylic polymer material according to claim 1, wherein the mixture of monomers comprises at least 80 wt % of acrylic or methacrylic monomers.

3. The acrylic polymer material according to claim 1, wherein the mixture of monomers comprises at least:
   an arylalkoxy-acrylate or an arylalkoxy-methacrylate;
   a hydroxylated acrylate and a hydroxylated methacrylate;
   an ethoxylated diol diacrylate and an ethoxylated diol dimethacrylate; and
   cinnamic alcohol.

4. The acrylic polymer material according to claim 3, wherein the arylalkoxy-acrylate or arylalkoxy-methacrylate is a compound chosen from the group consisting of ethoxylated phenoxy-acrylates comprising from one to six ethoxylated functions, 2-phenoxy-(2-ethoxy)$_n$-acrylate with $1 \leq n \leq 6$, 2-phenoxy-ethylacrylate, 2-phenoxy-(2-ethoxy)4-acrylate, 2-phenoxy-ethylmethacrylate, 2-phenoxy-2-ethoxy-ethylmethacrylate and 2-phenoxy-2-ethoxy-2-ethoxy-ethylmethacrylate, or a mixture of several of these compounds.

5. The acrylic polymer material according to claim 4, wherein the arylalkoxy-acrylate or the arylalkoxy-methacrylate is a mixture of 2-phenoxy-ethyl acrylate (2PEA) and 2-phenoxy-(2-ethoxy)4-acrylate (4PEA).

6. The acrylic polymer material according to claim 3, wherein the arylalkoxy-acrylate or the arylalkoxy-methacrylate makes up between 50 and 90 wt % of the mixture of monomers.

7. The acrylic polymer material according to claim 3, wherein the hydroxylated acrylate is a dihydroxy-alkyl monoacrylate or a dihydroxy-ethoxy-alkyl monoacrylate whose glycol alkyl chain comprises from 2 to 6 carbon atoms, 4-hydroxy-butyl-acrylate, hydroxy-ethyl-acrylate, hexanediol monoacrylate, or triethylene glycol monoacrylate; and in that the hydroxylated methacrylate is a dihydroxy-alkyl monomethacrylate or a dihydroxy-ethoxy-alkyl monomethacrylate whose glycol alkyl chain includes from 2 to 6 carbon atoms, hydroxy-ethyl-methacrylate, propanediol monomethacrylate, butanediol monomethacrylate, hexanediol monomethacrylate or triethylene glycol monomethacrylate.

8. The acrylic polymer material according to claim 3, wherein the hydroxylated alkylate and the hydroxylated methacrylate together make up between 8 and 35 wt % of the monomer mixture.

9. The acrylic polymer material according to claim 3, wherein the ethoxylated diol diacrylate and the ethoxylated diol dimethacrylate are polyethylene glycol diesters comprising from 2 to 5 ethoxylated functions.

10. The acrylic polymer material according to claim 3, wherein the ethoxylated diol diacrylate and the ethoxylated diol dimethacrylate together make up between 1 and 3 wt % of the mixture of monomers.

11. The acrylic polymer material according to claim 1, wherein the cinnamic alcohol makes up between 0.1 wt % and 5 wt % of the monomer mixture.

12. The acrylic polymer material according to claim 1, wherein the mixture of monomers further comprises a UV-absorbing monomer.

13. A method for manufacturing an acrylic polymer material according to claim 1, wherein said method comprises the following steps:
   producing a mixture of monomers containing at least 50 wt % of acrylic or methacrylic monomers and cinnamic alcohol, this mixture comprising at least one crosslinking monomer;
   adding at least one initiator compound to said mixture;
   performing radical polymerization of said mixture, in a single polymerization step, so as to obtain, through this polymerization, an acrylic or methacrylic copolymer that is crosslinked, viscoelastic, flexible and deformable at room temperature, and comprising cinnamic alcohol.

14. The method according to claim 13, further comprising a purification step.

15. An intraocular lens comprising an acrylic polymer material according to claim 1.

16. The acrylic polymer material according to claim 1, wherein the mixture of monomers comprises at least 90 wt % of acrylic or methacrylic monomers.

17. The acrylic polymer material according to claim 3, wherein the arylalkoxy-acrylate or the arylalkoxy-methacrylate makes up between 70 and 85 wt % of the mixture of monomers.

18. The acrylic polymer material according to claim 3, wherein the hydroxylated alkylate and the hydroxylated methacrylate together make up between 15 and 30 wt % of the monomer mixture.

19. The acrylic polymer material according to claim 1, wherein the cinnamic alcohol makes up between 0.2 wt % and 2 wt % of the monomer mixture.

20. The acrylic polymer material according to claim 1, wherein the cinnamic alcohol makes up about 0.5 wt % of the monomer mixture.

* * * * *